(12) United States Patent
Smith et al.

(10) Patent No.: US 7,220,764 B2
(45) Date of Patent: May 22, 2007

(54) SPHINGOSINE KINASE INHIBITORS

(75) Inventors: Charles D. Smith, Hummelstown, PA (US); Kevin J. French, Harrisburg, PA (US); Jong K. Yun, Hummelston, PA (US)

(73) Assignee: The Pennsylvania State University Research Foundation, University Park, PA (US)

( * ) Notice: Subject to any disclaimer, the term of this patent is extended or adjusted under 35 U.S.C. 154(b) by 0 days.

(21) Appl. No.: 10/462,954

(22) Filed: Jun. 17, 2003

(65) Prior Publication Data

US 2004/0034075 A1 Feb. 19, 2004

Related U.S. Application Data

(60) Provisional application No. 60/432,511, filed on Jun. 17, 2002.

(51) Int. Cl.
*A61K 31/426* (2006.01)
(52) U.S. Cl. .................. 514/365; 514/369; 514/370
(58) Field of Classification Search ............. 514/365, 514/369, 370
See application file for complete search history.

(56) References Cited

FOREIGN PATENT DOCUMENTS

| EP | 0 722 729 A | | 7/1996 |
|---|---|---|---|
| WO | 00/17175 | * | 3/2000 |
| WO | 01/64674 | * | 9/2001 |
| WO | 01/74793 | * | 10/2001 |

OTHER PUBLICATIONS

Zimenkovsky et al., Fiziologichno Aktivni Rechovini, 2, (2002) 58-64.*
Caceres-Dittmar et al., Clinical and Experimental Immunology, (1993), 91(3), pp. 500-505.*
Rubbert et al., International Journal of Cancer, (1991), 49(1), pp. 25-31 (abstract).*
Perfetti et al., Experimental Hematology, (1991), 19(6), pp. 549 (abstract).*
Kono et al. S-15183a and b, "New Sphingosine Kinase Inhibitors, Produced by a Fungus," *The Journal of Antibiotics*, vol. 54, No. 5, 2001, pp. 415-420.

* cited by examiner

*Primary Examiner*—Phyllis G. Spivack
(74) *Attorney, Agent, or Firm*—McDonnell Boehnen Hulbert & Berghoff LLP

(57) ABSTRACT

The invention relates to compositions and methods for inhibiting sphingosine kinase and for treating hyperproliferative disease.

8 Claims, 4 Drawing Sheets

DMSO (control, ■)
Compound 5 at a dose of 75 mg/kg (▲)

SPHINGOSINE KINASE INHIBITORS

CROSS REFERENCE TO RELATED APPLICATIONS

This application claims priority from U.S. Provisional Application Ser. No. 60/432,511, filed Jun. 17, 2002, which is incorporated herein by reference in its entirety.

STATEMENT OF GOVERNMENT INTEREST

This invention was made with Government support under NIH grant no. R24 CA788243. The Government may have certain rights in the invention.

BACKGROUND OF THE INVENTION

1. Field of the Invention

The invention relates to compounds that are capable of inhibiting sphingosine kinase and that are useful for treating or preventing hyperproliferative disease, autoimmune disease, inflammatory disease, or allergy. The invention also relates to methods and compositions for treating or preventing hyperproliferative disease, autoimmune disease, inflammatory disease, or allergy.

2. Description of the Related Art

The mechanisms and effects of the interconversion of sphingolipids have been the subjects of a growing body of scientific investigation. Sphingomyelin, for example, is not only a building block for cellular membranes but also serves as the precursor for potent lipid messengers that have profound cellular effects. Stimulus-induced metabolism of these lipids is critically involved in cancer cell biology. Consequently, these metabolic pathways offer exciting new molecular targets for the development of anticancer drugs.

As depicted in FIG. 1, ceramide is produced by the hydrolysis of sphingomyelin in response to stresses including chemotherapeutic drugs. Ceramide induces apoptosis in proliferating cells by a mechanism that remains to be elucidated. However, ceramide can be further hydrolyzed by the action of ceramidase to produce sphingosine, which is then rapidly phosphorylated by sphingosine kinase (SK) in many different cell types to produce sphingosine-1-phosphate (S1P). The actions of ceramidase and SK appear to be rapidly activated by a number of growth factors. A critical balance between the concentrations of ceramide and S1P, termed the ceramide/S1P rheostat, has been hypothesized to determine the fate (proliferation or apoptosis) of the cell. In this view, it is the balance between the cellular concentrations of ceramide and S1P that determines whether a cell proliferates or undergoes apoptosis.

Upon exposure to mitogens or intracellular oncoproteins, cells experience a rapid increase in the intracellular levels of S1P and depletion of ceramide levels, and consistent with the hypothesis, this "setting" of the rheostat promotes cell survival and proliferation. In contrast, activation of sphingomyelinase in the absence of activation of ceramidase and SK results in the accumulation of ceramide and subsequent apoptosis. Importantly, ceramide appears to induce apoptosis in tumor cells without disrupting quiescent normal cells. Furthermore, ceramide enhances apoptosis in response to anticancer drugs including Taxol and etoposide.

Accumulating evidence confirms that S1P is a critical second messenger that exerts proliferative and antiapoptotic actions. For example, microinjection of S1P into mouse oocytes induces DNA synthesis, and promotes the secretion of Insulin-like Growth Factor-II (IGF-II) from human breast carcinoma cells. Additionally, it has been shown that S1P effectively inhibits ceramide-induced apoptosis in association with decreased caspase activation. These studies in various cell lines consistently indicate that S1P is able to induce proliferation and protect cells from ceramide-induced apoptosis. While the elucidation of downstream targets of S1P remains an interesting problem in cell biology, sufficient validation of these pathways has been established to justify their evaluation as targets for new types of anticancer drugs. As S1P appears to be the most direct mitogenic messenger, inhibition of its production should have profound antiproliferative effects on tumor cells.

Sphingosine kinase (SK) is the sole enzyme responsible for S1P production in cells. The enzyme was initially isolated from rat kidney, and demonstrated $K_M$ values 5 µM and 93 µM for sphingosine and ATP, respectively. The human isoform was cloned in 2000, and displays similar physical and biochemical characteristics. Shortly thereafter, a second SK isoform was cloned: however, this species displays much lower activity and different kinetic profiles than the type 1 enzyme. RNA encoding SK is detected in most tissues, with higher levels in lung and spleen. Interestingly, a number of studies have shown that a variety of proliferative factors, including protein kinase C (PKC) activators, fetal calf serum and platelet-derived growth factor, epidermal growth factor (EGF), and tumor necrosis factor-alpha (TNF-α) rapidly elevate cellular SK activity.

Recently, an oncogenic role of SK has been directly demonstrated. In these studies, transfection of SK into NIH 3T3 fibroblasts was sufficient to promote foci formation and cell growth in soft-agar, and to allow these cells to form tumors in NOD/SCID mice. Additionally, inhibition of SK by transfection with a dominant-negative SK mutant or by treatment of cells with the nonspecific SK inhibitor D-erythro-N,N-dimethylsphingosine blocked transformation mediated by oncogenic H-Ras. Since abnormal activation of Ras as well as overexpression and mutation of ras family genes frequently occurs in cancer, these findings suggest a significant role of SK in this disease. Another study showed that a cellular receptor that specifically binds S1P, termed EDG4, is a specific marker for ovarian cancer cells. S1P has also been implicated in angiogenesis, as it induces motility and mitogenesis in smooth muscle cells and endothelial cell differentiation. These various findings indicate that SK is an important molecular target in cancer.

Despite the high level of interest in sphingolipid-derived signaling, there are very few demonstrated inhibitors of the enzymes of this pathway. In particular, the field suffers from a lack of potent and selective inhibitors of SK. Pharmacological studies to date have used three compounds to inhibit SK activity: D-erythro-N,N-dimethylsphingosine, D,L-threo-dihydrosphingosine and N,N,N-trimethyl-sphingosine. However, these compounds are not specific inhibitors of SK and have been shown to affect other important cellular proteins, including PKC, sphingosine-dependent protein kinase, 3-phosphoinositide-dependent kinase, and casein kinase II. Therefore, there is a need in the art for selective and potent inhibitors of SK as antiproliferative and anti-inflammatory agents.

BRIEF SUMMARY OF THE INVENTION

The invention provides compounds of formula (I), formula (II), formula (III), formula (IV), formula (V), formula (VI), formula (VII), formula (VIII), formula (IX), formula (X), and formula (XI), shown below, pharmaceutical compositions containing such compounds and methods employing such compounds or compositions in the treatment or prevention of hyperproliferative disease, autoimmune disease, inflammatory disease, or allergy, and more specifically compounds that are capable of inhibiting SK.

In one aspect, the invention provides compounds of formula (I):

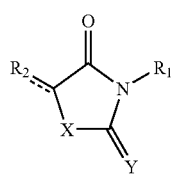

(I)

and pharmaceutically acceptable salts thereof, wherein
X is $CHR_3$ or S;
Y is O or S;
$R_1$ and $R_2$ are independently H, $(C_1-C_{15})$ alkyl, cycloalkyl, —$C_1$–$C_6$ alkyl-($C_3$–$C_7$)cycloalkyl, aryl, —$C_1$–$C_6$ alkyl-aryl, —$C_2$–$C_6$ alkenyl-aryl, heteroaryl, —$C_1$–$C_6$ alkyl-heteroaryl, heterocycloalkyl, —$C_1$–$C_6$ alkyl-heterocycloalkyl, halogen, haloalkyl, —OH, $C_1$–$C_6$ alkoxy, hydroxyalkyl, alkanoyl, —COOH, carbamoyl, mono or dialkylaminocarbamoyl, —SH, —S-alkyl, —$CF_3$, —$OCF_3$, —$NO_2$, —$NH_2$, —$CO_2R_3$, —$OC(O)R_3$, mono or dialkylcarbamoyl, mono or dialkylamino, aminoalkyl, mono- or dialkylaminoalkyl, thiocarbamoyl, or mono or dialkylthiocarbamoyl; and $R_3$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently $(C_1-C_6)$ alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or $(C_1-C_6)$ alkyl.

The invention also provides compounds of formula II:

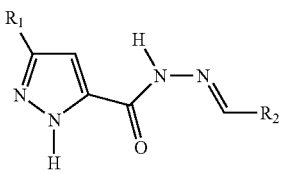

(II)

and pharmaceutically acceptable salts thereof, wherein
$R_1$ and $R_2$ are independently H, $(C_1-C_{15})$ alkyl, cycloalkyl, —$C_1$–$C_6$ alkyl-($C_3$–$C_7$)cycloalkyl, aryl, —$C_1$–$C_6$ alkyl-aryl, heteroaryl, —$C_1$–$C_6$ alkyl-heteroaryl, heterocycloalkyl, —$C_1$–$C_6$ alkyl-heterocycloalkyl, halogen, haloalkyl, —OH, $C_1$–$C_6$ alkoxy, hydroxyalkyl, alkanoyl, —COOH, carbamoyl, mono or dialkylaminocarbamoyl, —SH, —S-alkyl, —$CF_3$, —$OCF_3$, —$NO_2$, —$NH_2$, —$CO_2R_8$, —$OC(O)R_8$, mono or dialkylcarbamoyl, mono or dialkylamino, aminoalkyl, mono- or dialkylaminoalkyl, thiocarbamoyl, or mono or dialkylthiocarbamoyl; and $R_8$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently $(C_1-C_6)$ alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or $(C_1-C_6)$ alkyl.

The invention further provides compounds of formula (III):

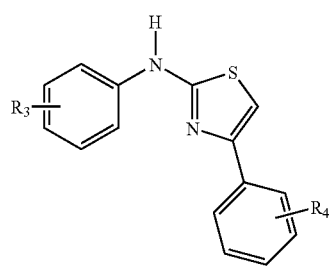

(III)

and pharmaceutically acceptable salts thereof, wherein
$R_3$ and $R_4$ are independently H, $(C_1-C_{15})$ alkyl, cycloalkyl, —$C_1$–$C_6$ alkyl-($C_3$–$C_7$)cycloalkyl, aryl, —$C_1$–$C_6$ alkyl-aryl, —$C_2$–$C_6$ alkenyl-aryl, heteroaryl, —$C_1$–$C_6$ alkyl-heteroaryl, heterocycloalkyl, —$C_1$–$C_6$ alkyl-heterocycloalkyl, halogen, haloalkyl, —OH, $C_1$–$C_6$ alkoxy, hydroxyalkyl, alkanoyl, —COOH, carbamoyl, mono or dialkylaminocarbamoyl, —SH, —S-alkyl, —$CF_3$, —$OCF_3$, —$NO_2$, —$NH_2$, —$CO_2R_8$, —$OC(O)R_8$, mono or dialkylcarbamoyl, mono or dialkylamino, aminoalkyl, mono- or dialkylaminoalkyl, thiocarbamoyl, or mono or dialkylthiocarbamoyl; and $R_8$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently $(C_1-C_6)$ alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or $(C_1-C_6)$ alkyl.

The invention further provides compounds of formula (IV):

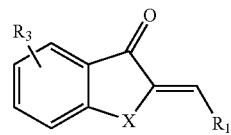

(IV)

and pharmaceutically acceptable salts thereof, wherein
X is O or S;
$R_1$ and $R_3$ are independently H, $(C_1-C_{15})$ alkyl, cycloalkyl, —$C_1$–$C_6$ alkyl-($C_3$–$C_7$)cycloalkyl, aryl, —$C_1$–$C_6$ alkyl-aryl, —$C_2$–$C_6$ alkenyl-aryl, heteroaryl, —$C_1$–$C_6$ alkyl-heteroaryl, heterocycloalkyl, —$C_1$–$C_6$ alkyl-heterocycloalkyl, halogen, haloalkyl, —OH, $C_1$–$C_6$ alkoxy, hydroxyalkyl, alkanoyl, —COOH, carbamoyl, mono or dialkylaminocarbamoyl, —SH, —S-alkyl, —$CF_3$, —$OCF_3$, —$NO_2$, —$NH_2$, —$CO_2R_8$, —$OC(O)R_8$, mono or dialkylcarbamoyl, mono or dialkylamino, aminoalkyl, mono- or dialkylaminoalkyl, thiocarbamoyl, or mono or dialkylthiocarbamoyl; and $R_8$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently $(C_1-C_6)$ alkyl, halogen, haloalkyl, —$CF_3$, —$OCF_3$, —OH, $C_1-C_6$ alkoxy, hydroxyalkyl, —CN, —$CO_2H$, —SH, —S-alkyl, —$NO_2$, or NR'R", wherein R' and R" are independently H or $(C_1-C_6)$ alkyl.

The invention further provides compounds of formula (V):

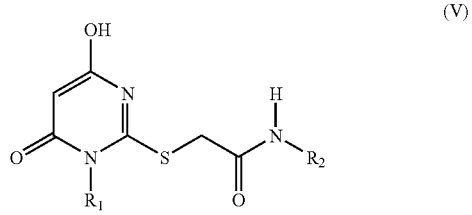

(V)

and pharmaceutically acceptable salts thereof, wherein $R_1$ and $R_2$ are independently H, $(C_1-C_{15})$ alkyl, cycloalkyl, —$C_1-C_6$ alkyl-$(C_3-C_7)$cycloalkyl, aryl, —$C_1-C_6$ alkyl-aryl, —$C_2-C_6$ alkenyl-aryl, heteroaryl, —$C_1-C_6$ alkyl-heteroaryl, heterocycloalkyl, —$C_1-C_6$ alkyl-heterocycloalkyl, halogen, haloalkyl, —OH, $C_1-C_6$ alkoxy, hydroxyalkyl, alkanoyl, —COOH, carbamoyl, mono or dialkylaminocarbamoyl, —SH, —S-alkyl, —$CF_3$, —$OCF_3$, —$NO_2$, —$NH_2$, —$CO_2R_8$, —$OC(O)R_8$, mono or dialkylcarbamoyl, mono or dialkylamino, aminoalkyl, mono- or dialkylaminoalkyl, thiocarbamoyl, or mono or dialkylthiocarbamoyl; and $R_8$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently $(C_1-C_6)$ alkyl, halogen, haloalkyl, —$CF_3$, —$OCF_3$, —OH, $C_1-C_6$ alkoxy, hydroxyalkyl, —CN, —$CO_2H$, —SH, —S-alkyl, —$NO_2$, or NR'R", wherein R' and R" are independently H or $(C_1-C_6)$ alkyl.

The invention further provides compounds of formula (VI):

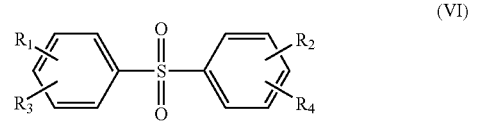

(VI)

and pharmaceutically acceptable salts thereof, wherein $R_1$, $R_2$, $R_3$, and $R_4$ are independently H, $(C_1-C_{15})$ alkyl, cycloalkyl, —$C_1-C_6$ alkyl-$(C_3-C_7)$cycloalkyl, aryl, —$C_1-C_6$ alkyl-aryl, —$C_2-C_6$ alkenyl-aryl, heteroaryl, —$C_1-C_6$ alkyl-heteroaryl, heterocycloalkyl, —$C_1-C_6$ alkyl-heterocycloalkyl, halogen, haloalkyl, —OH, $C_1-C_6$ alkoxy, hydroxyalkyl, alkanoyl, —COOH, carbamoyl, mono or dialkylaminocarbamoyl, —SH, —S-alkyl, —$CF_3$, —$OCF_3$, —$NO_2$, —$NH_2$, —$CO_2R_8$, —$OC(O)R_8$, mono or dialkylcarbamoyl, mono or dialkylamino, aminoalkyl, mono- or dialkylaminoalkyl, thiocarbamoyl, or mono or dialkylthiocarbamoyl; and $R_8$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently $(C_1-C_6)$ alkyl, halogen, haloalkyl, —$CF_3$, —$OCF_3$, —OH, $C_1-C_6$ alkoxy, hydroxyalkyl, —CN, —$CO_2H$, —SH, —S-alkyl, —$NO_2$, or NR'R", wherein R' and R" are independently H or $(C_1-C_6)$ alkyl.

The invention also provides compounds of formula (VII):

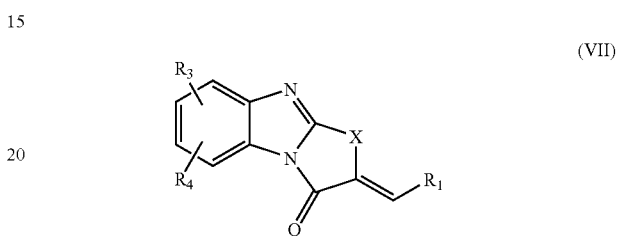

(VII)

and pharmaceutically acceptable salts thereof, wherein

X is O or S;

$R_1$, $R_3$ and $R_4$ are independently H, $(C_1-C_{15})$ alkyl, cycloalkyl, —$C_1-C_6$ alkyl-$(C_3-C_7)$cycloalkyl, aryl, —$C_1-C_6$ alkyl-aryl, —$C_2-C_6$ alkenyl-aryl, heteroaryl, —$C_1-C_6$ alkyl-heteroaryl, heterocycloalkyl, —$C_1-C_6$ alkyl-heterocycloalkyl, halogen, haloalkyl, —OH, $C_1-C_6$ alkoxy, hydroxyalkyl, alkanoyl, —COOH, carbamoyl, mono or dialkylaminocarbamoyl, —SH, —S-alkyl, —$CF_3$, —$OCF_3$, —$NO_2$, —$NH_2$, —$CO_2R_8$, —$OC(O)R_8$, mono or dialkylcarbamoyl, mono or dialkylamino, aminoalkyl, mono- or dialkylaminoalkyl, thiocarbamoyl, or mono or dialkylthiocarbamoyl; and $R_8$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently $(C_1-C_6)$ alkyl, halogen, haloalkyl, —$CF_3$, —$OCF_3$, —OH, $C_1-C_6$ alkoxy, hydroxyalkyl, —CN, —$CO_2H$, —SH, —S-alkyl, —$NO_2$, or NR'R", wherein R' and R" are independently H or $(C_1-C_6)$ alkyl.

The invention also provides compounds of formula (VIII):

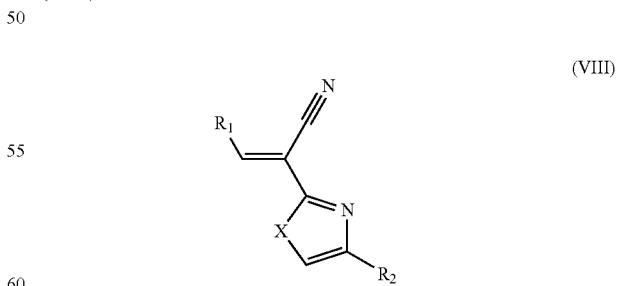

(VIII)

and pharmaceutically acceptable salts thereof, wherein

X is O or S;

$R_1$, and $R_2$ are independently H, $(C_1-C_{15})$ alkyl, cycloalkyl, —$C_1-C_6$ alkyl-$(C_3-C_7)$cycloalkyl, aryl, —$C_1-C_6$ alkyl-aryl, —$C_2-C_6$ alkenyl-aryl, heteroaryl, —$C_1-C_6$ alkyl-heteroaryl, heterocycloalkyl, —C$_1$–C$_6$ alkyl-heterocycloalkyl, halogen, haloalkyl, —OH, C$_1$–C$_6$ alkoxy, hydroxyalkyl, alkanoyl, —COOH, carbamoyl, mono or dialkylaminocarbamoyl, —SH, —S-alkyl, —CF$_3$, —OCF$_3$, —NO$_2$, —NH$_2$, —CO$_2$R$_8$, —OC(O)R$_8$, mono or dialkylcarbamoyl, mono or dialkylamino, aminoalkyl, mono- or dialkylaminoalkyl, thiocarbamoyl, or mono or dialkylthiocarbamoyl; and R$_8$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl.

The invention also provides compounds of formula (IX):

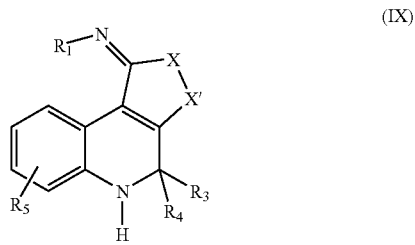

(IX)

and pharmaceutically acceptable salts thereof, wherein

X and X' are independently O or S;

R$_1$, R$_3$, R$_4$ and R$_5$ are independently H, (C$_1$–C$_{15}$) alkyl, cycloalkyl, —C$_1$–C$_6$ alkyl-(C$_3$–C$_7$)cycloalkyl, aryl, —C$_1$–C$_6$ alkyl-aryl, —C$_2$–C$_6$ alkenyl-aryl, heteroaryl, —C$_1$–C$_6$ alkyl-heteroaryl, heterocycloalkyl, —C$_1$–C$_6$ alkyl-heterocycloalkyl, halogen, haloalkyl, —OH, C$_1$–C$_6$ alkoxy, hydroxyalkyl, alkanoyl, —COOH, carbamoyl, mono or dialkylaminocarbamoyl, —SH, —S-alkyl, —CF$_3$, —OCF$_3$, —NO$_2$, —NH$_2$, —CO$_2$R$_8$, —OC(O)R$_8$, mono or dialkylcarbamoyl, mono or dialkylamino, aminoalkyl, mono- or dialkylaminoalkyl, thiocarbamoyl, or mono or dialkylthiocarbamoyl; and R$_8$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl.

The invention also provides compounds of formula (X):

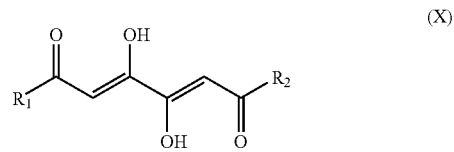

(X)

and pharmaceutically acceptable salts thereof, wherein

R$_1$ and R$_2$ are independently H, (C$_1$–C$_{15}$) alkyl, cycloalkyl, —C$_1$–C$_6$ alkyl-(C$_3$–C$_7$)cycloalkyl, aryl, —C$_1$–C$_6$ alkyl-aryl, —C$_2$–C$_6$ alkenyl-aryl, heteroaryl, —C$_1$–C$_6$ alkyl-heteroaryl, heterocycloalkyl, —C$_1$–C$_6$ alkyl-heterocycloalkyl, halogen, haloalkyl, —OH, C$_1$–C$_6$ alkoxy, hydroxyalkyl, alkanoyl, —COOH, carbamoyl, mono or dialkylaminocarbamoyl, —SH, —S-alkyl, —CF$_3$, —OCF$_3$, —NO$_2$, —NH$_2$, —CO$_2$R$_8$, —OC(O)R$_8$, mono or dialkylcarbamoyl, mono or dialkylamino, aminoalkyl, mono- or dialkylaminoalkyl, thiocarbamoyl, or mono or dialkylthiocarbamoyl; and R$_8$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl.

The invention also provides compounds of formula (XI):

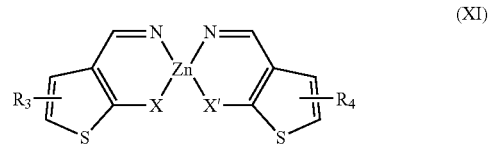

(XI)

and pharmaceutically acceptable salts thereof, wherein

X and X' are independently O or S;

R$_3$ and R$_4$ are independently H, (C$_1$–C$_{15}$) alkyl, cycloalkyl, —C$_1$–C$_6$ alkyl-(C$_3$–C$_7$)cycloalkyl, aryl, —C$_1$–C$_6$ alkyl-aryl, —C$_2$–C$_6$ alkenyl-aryl, heteroaryl, —C$_1$–C$_6$ alkyl-heteroaryl, heterocycloalkyl, —C$_1$–C$_6$ alkyl-heterocycloalkyl, halogen, haloalkyl, —OH, C$_1$–C$_6$ alkoxy, hydroxyalkyl, alkanoyl, COOH, carbamoyl, mono or dialkylaminocarbamoyl, —SH, —S-alkyl, —CF$_3$, —OCF$_3$, —NO$_2$, —NH$_2$, —CO$_2$R$_8$, —OC(O)R$_8$, mono or dialkylcarbamoyl, mono or dialkylamino, aminoalkyl, mono- or dialkylaminoalkyl, thiocarbamoyl, or mono or dialkylthiocarbamoyl; and R$_8$ is H, alkyl, aryl, arylalkyl, cycloalkyl, cycloalkylalkyl, heteroaryl, heteroarylalkyl, heterocycloalkyl, or heterocycloalkylalkyl;

wherein the alkyl and ring portion of each of the above substituents is optionally substituted with up to 5 groups that are independently (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl.

The invention also provides pharmaceutical compositions comprising a compound or salt of formulae I, II, III, IV, V, VI, VII, VIII, IX, X, or XI, and at least one pharmaceutically acceptable carrier, solvent, adjuvant or diluent.

The invention also provides methods for the treatment or prevention of hyperproliferative disease, autoimmune disease, inflammatory disease, or allergy, comprising administering a therapeutically-effective amount of a pharmaceutical formulation of a compound or salt of formulae I, II, III, IV, V, VI, VII, VIII, IX, X, or XI, and at least one pharmaceutically acceptable carrier, solvent, adjuvant or diluent to an animal in need thereof.

The invention also provides the use of a compound or salt according to formula I, II, III, IV, V, VI, VII, VIII, IX, X, or XI for the manufacture of a medicament for treating a hyperproliferative disease, autoimmune disease, inflammatory disease, or allergy.

Specific preferred embodiments of the present invention will become evident from the following more detailed description of certain preferred embodiments and the claims.

DETAILED DESCRIPTION OF PREFERRED EMBODIMENTS

Figure 1:
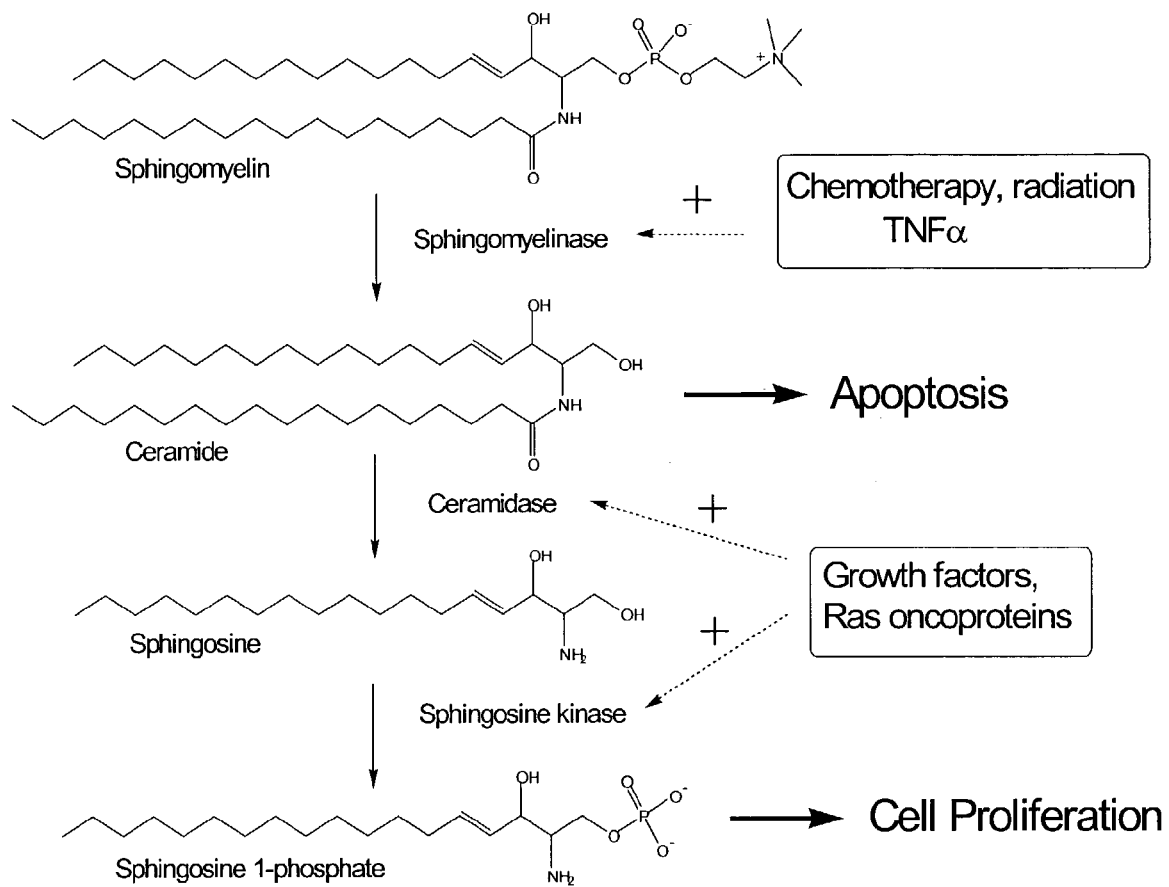
FIG. 1 is a chemical scheme depicting the metabolism of sphingolipids.

Unless the substituents for a particular formula are expressly defined for that formula, they are understood to carry the definitions set forth in connection with the preceding formula to which the particular formula makes reference.

As noted above, the invention provides compounds of formula I:

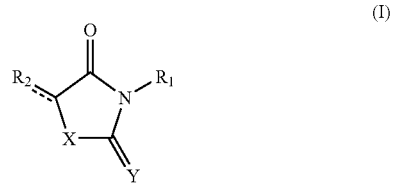

(I)

Preferred compounds of formula I include those of formula I-1:

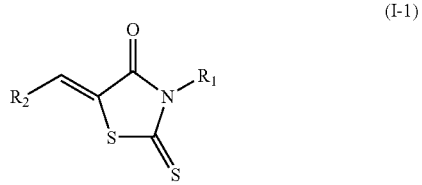

(I-1)

wherein
$R_1$ is cycloalkyl, aryl, heteroaryl or heterocycloalkyl, wherein each ring is optionally substituted with 1, 2, or 3 groups that are independently ($C_1$–$C_6$) alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl; and
$R_2$ is cycloalkyl, aryl, heteroaryl or heterocycloalkyl, wherein each ring is optionally substituted with 1, 2, or 3 groups that are independently ($C_1$–$C_6$) alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl.

Preferred compounds of the formula I-1 include those wherein
$R_1$ is aryl optionally substituted with 1, or 2 groups that are independently halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl; and
$R_2$ is aryl optionally substituted with 1, or 2 groups that are independently halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl.

Preferred compounds of the formula I-1 include those wherein
$R_1$ is phenyl optionally substituted with 1 or 2 groups that are independently halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl; and
$R_2$ is phenyl optionally substituted with 1 or 2 groups that are independently halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl.

Preferred compounds of the formula I-1 include those wherein $R_1$ is phenyl substituted with one or two $C_1$–$C_6$ alkoxy groups.

Preferred compounds of the formula I-1 include those wherein $R_2$ is phenyl substituted with 1 or 2 of —OH.

As noted above, the invention also provides compounds of formula II:

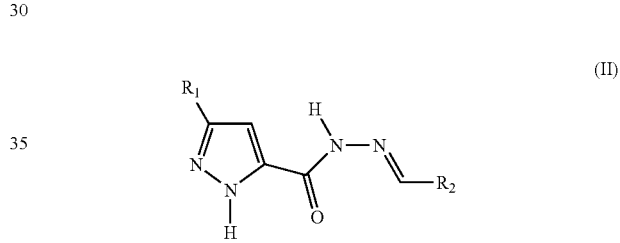

(II)

Preferred compounds of formula (II) include those of formula II-1, i.e., compounds of formula (II) wherein:
$R_1$ is cycloalkyl, aryl, heteroaryl or heterocycloalkyl, wherein each ring is optionally substituted with 1, 2, or 3 groups that are independently ($C_1$–$C_6$) alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl; and
$R_2$ is cycloalkyl, aryl, heteroaryl or heterocycloalkyl, wherein each ring is optionally substituted with 1, 2, or 3 groups that are independently ($C_1$–$C_6$) alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl.

Preferred compounds of the formula II-1 include those wherein
$R_1$ is aryl optionally substituted with 1 or 2 groups that are independently halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl; and
$R_2$ is aryl optionally substituted with 1 or 2 groups that are independently halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl.

Preferred compounds of the formula II-1 include those wherein
R$_1$ is biphenyl optionally substituted with 1 or 2 groups that are independently halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl; and
R$_2$ is biphenyl optionally substituted with 1 or 2 groups that are independently halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl.

Preferred compounds of the formula II-1 include those wherein R$_1$ is biphenyl.

Preferred compounds of the formula II-1 include those wherein R$_2$ is biphenyl substituted with 1 or 2 of —OH.

As noted above, the invention further provides compounds of formula III:

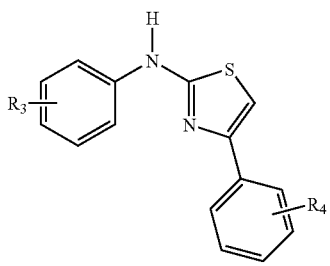

(III)

Preferred compounds of formula (III) include those of formula III-1, i.e., compounds of formula (III) wherein:
R$_3$ is H, (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl; and.
R$_4$ is H, (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl.

Preferred compounds of the formula III-1 include those wherein
R$_3$ is H, halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl; and
R$_4$ is H, halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl.

Preferred compounds of the formula III-1 include those wherein R$_3$ is —OH.

Preferred compounds of the formula III-1 include those wherein R$_4$ is halogen.

As noted above, the invention further provides compounds of formula (IV):

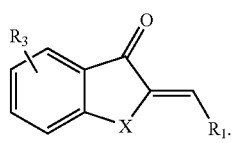

(IV)

Preferred compounds of formula (IV) include those of formula IV-1, i.e., compounds of formula (IV) wherein:
X is oxygen;
R$_1$ is cycloalkyl, aryl, heteroaryl or heterocycloalkyl, wherein each ring is optionally substituted with 1, 2, or 3 groups that are independently (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl; and
R$_3$ is H, (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl.

Preferred compounds of the formula IV-1 include those wherein
R$_1$ is aryl optionally substituted with 1, or 2 groups that are independently halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl; and
R$_3$ is H, halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl.

Preferred compounds of the formula IV-1 include those wherein
R$_1$ is phenyl optionally substituted with 1 or 2 groups that are independently halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl; and
R$_3$ is H, halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl.

Preferred compounds of the formula IV-1 include those wherein R$_1$ is phenyl substituted with one or two —OH groups.

Preferred compounds of the formula IV-1 include those wherein R$_3$ is H.

Preferred compounds of formula (IV) include those of formula IV-2, i.e., compounds of formula (IV) wherein:
X is sulfur;
R$_1$ is cycloalkyl, aryl, heteroaryl or heterocycloalkyl, wherein each ring is optionally substituted with 1, 2, or 3 groups that are independently (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl; and
R$_3$ is H, (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl.

Preferred compounds of the formula IV-2 include those wherein
R$_1$ is aryl optionally substituted with 1, or 2 groups that are independently halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl; and
R$_3$ is H, halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl.

Preferred compounds of the formula IV-2 include those wherein
R$_1$ is phenyl optionally substituted with 1 or 2 groups that are independently halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl; and $R_3$ is H, halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl.

Preferred compounds of the formula IV-2 include those wherein $R_1$ is phenyl substituted with one or two —OH groups.

Preferred compounds of the formula IV-2 include those wherein $R_3$ is H.

As noted above, the invention also provides compounds of formula (V):

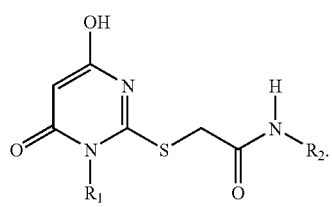

(V)

Preferred compounds of formula (V) include those of formula V-1, i.e., compounds of formula (V) wherein:

$R_1$ is cycloalkyl, aryl, heteroaryl or heterocycloalkyl, wherein each ring is optionally substituted with 1, 2, or 3 groups that are independently ($C_1$–$C_6$) alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl; and $R_2$ is cycloalkyl, aryl, heteroaryl or heterocycloalkyl, wherein each ring is optionally substituted with 1, 2, or 3 groups that are independently ($C_1$–$C_6$) alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl.

Preferred compounds of the formula V-1 include those wherein $R_1$ is aryl optionally substituted with 1 or 2 groups that are independently halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl; and $R_2$ is heteroaryl optionally substituted with 1 or 2 groups that are independently halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl.

Preferred compounds of the formula V-1 include those wherein $R_1$ is phenyl optionally substituted with 1 or 2 groups that are independently halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl; and $R_2$ is benzothiazolyl optionally substituted with 1 or 2 groups that are independently halogen, —$CF_3$, —$OCF_3$, —OH, $C_1$–$C_6$ alkoxy, —CN, —$CO_2H$, —SH, —$NO_2$, or NR'R", wherein R' and R" are independently H or ($C_1$–$C_6$) alkyl.

Preferred compounds of the formula V-1 include those wherein $R_1$ is phenyl substituted with $C_1$–$C_6$ alkoxy.

Preferred compounds of the formula V-1 include those wherein $R_2$ is benzothiazolyl.

As noted above, the invention also provides compounds of formula (VI):

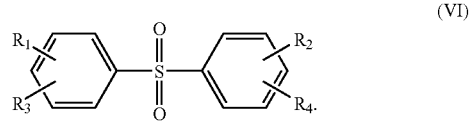

(VI)

Preferred compounds of formula (VI) include those of formula VI-1, i.e., compounds of formula (VI) wherein:

$R_1$ is H;

$R_2$ is H, cycloalkyl, aryl, heteroaryl or heterocycloalkyl, wherein each ring is optionally substituted with 1, 2, or 3 groups that are independently ($C_1$–$C_6$) alkyl, halogen, haloalkyl, —$CF_3$, —$CF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl;

$R_3$ and $R_4$ are independently H, ($C_1$–$C_6$) alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl.

Preferred compounds of the formula VI-1 include those wherein $R_2$ is cycloalkyl optionally substituted with 1, 2, or 3 groups that are independently ($C_1$–$C_6$) alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl;

$R_3$ and $R_4$ are independently ($C_1$–$C_6$) alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl.

Preferred compounds of the formula VI-1 include those wherein $R_2$ is adamantanyl optionally substituted with 1, 2, or 3 groups that are independently ($C_1$–$C_6$) alkyl, halogen, haloalkyl, —$CF_3$, —$OCF_3$, —OH, $C_1$–$C_6$ alkoxy, hydroxyalkyl, —CN, —$CO_2H$, —SH, —S-alkyl, —$NO_2$, or NR'R", wherein R' and R" are independently H or ($C_1$–$C_6$) alkyl;

$R_3$ and $R_4$ are independently halogen, —$CF_3$, —$OCF_3$, —OH, $C_1$–$C_6$ alkoxy, hydroxyalkyl, —CN, or —$CO_2H$.

Preferred compounds of the formula VI-1 include those wherein $R_2$ is adamantanyl.

Preferred compounds of the formula VI-1 include those wherein $R_3$ and $R_4$ are each —OH.

Preferred compounds of the formula VI-1 include those wherein $R_3$ and $R_4$ are each —ONa.

As noted above, the invention further provides compounds of formula (VII):

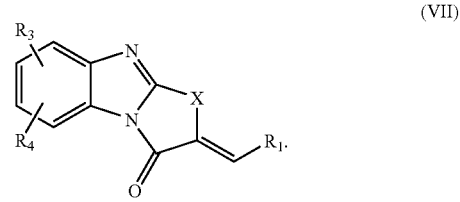

(VII)

Preferred compounds of formula (VII) include those of formula VII-1, i.e., compounds of formula (VII) wherein:

X is sulfur;

$R_1$ is cycloalkyl, aryl, heteroaryl or heterocycloalkyl, wherein each ring is optionally substituted with 1, 2, or 3 groups that are independently $(C_1-C_6)$ alkyl, halogen, haloalkyl, —$CF_3$, —$OCF_3$, —OH, $C_1-C_6$ alkoxy, hydroxyalkyl, —CN, —$CO_2H$, —SH, —S-alkyl, —$NO_2$, or NR'R", wherein R' and R" are independently H or $(C_1-C_6)$ alkyl; and $R_3$ and $R_4$ are independently H, $(C_1-C_6)$ alkyl, halogen, haloalkyl, —$CF_3$, —$OCF_3$, —OH, $C_1-C_6$ alkoxy, hydroxyalkyl, —CN, —$CO_2H$, —SH, —S-alkyl, —$NO_2$, or NR'R", wherein R' and R" are independently H or $(C_1-C_6)$ alkyl.

Preferred compounds of the formula VII-1 include those wherein $R_1$ is aryl optionally substituted with 1, 2 or 3 groups that are independently halogen, —$CF_3$, —$OCF_3$, —OH, $CL-C_6$ alkoxy, —CN, —$CO_2H$, —SH, —$NO_2$, or NR'R", wherein R' and R" are independently H or $(C_1-C_6)$ alkyl; and $R_3$ and $R_4$ are independently H, $(C_1-C_6)$ alkyl, halogen, —$CF_3$, —$OCF_3$, —OH, $C_1-C_6$ alkoxy, —CN, —$CO_2H$, —SH, —$NO_2$, or NR'R", wherein R' and R" are independently H or $(C_1-C_6)$ alkyl.

Preferred compounds of the formula VII-1 include those wherein $R_1$ is phenyl optionally substituted with 1, 2 or 3 groups that are independently halogen, —$CF_3$, —$OCF_3$, —OH, $C_1-C_6$ alkoxy, —CN, —$CO_2H$, —SH, —$NO_2$, or NR'R", wherein R' and R" are independently H or $(C_1-C_6)$ alkyl; and $R_3$ and $R_4$ are independently H, $(C_1-C_6)$ alkyl, halogen, —$CF_3$, —$OCF_3$, —OH, $C_1-C_6$ alkoxy, —CN, —$CO_2H$, —SH, —$NO_2$, or NR'R", wherein R' and R" are independently H or $(C_1-C_6)$ alkyl.

Preferred compounds of the formula VII-1 include those wherein $R_1$ is phenyl substituted with 1, 2, or 3 groups independently selected from halogen and —OH.

Preferred compounds of the formula VII-1 include those wherein $R_3$ and $R_4$ are independently $(C_1-C_6)$ alkyl.

As noted above, the invention further provides compounds of formula (VIII):

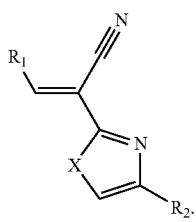

(VIII)

Preferred compounds of formula (VIII) include those of formula VIII-1, i.e., compounds of formula (VIII) wherein:

X is sulfur;

$R_1$ is cycloalkyl, aryl, heteroaryl or heterocycloalkyl, wherein each ring is optionally substituted with 1, 2, or 3 groups that are independently $(C_1-C_6)$ alkyl, halogen, haloalkyl, —$CF_3$, —$OCF_3$, —OH, $C_1-C_6$ alkoxy, hydroxyalkyl, —CN, —$CO_2H$, —SH, —S-alkyl, —$NO_2$, or NR'R", wherein R' and R" are independently H or $(C_1-C_6)$ alkyl; and $R_2$ is cycloalkyl, aryl, heteroaryl or heterocycloalkyl, wherein each ring is optionally substituted with 1, 2, or 3 groups that are independently $(C_1-C_6)$ alkyl, halogen, haloalkyl, —$CF_3$, —$OCF_3$, —OH, $C_1-C_6$ alkoxy, hydroxyalkyl, —CN, —$CO_2H$, —SH, —S-alkyl, —$NO_2$, or NR'R", wherein R' and R" are independently H or $(C_1-C_6)$ alkyl.

Preferred compounds of the formula VIII-1 include those wherein $R_1$ is aryl optionally substituted with 1 or 2 groups that are independently halogen, —$CF_3$, —$OCF_3$, —OH, $C_1-C_6$ alkoxy, —CN, —$CO_2H$, —SH, —$NO_2$, or NR'R", wherein R' and R" are independently H or $(C_1-C_6)$ alkyl; and $R_2$ is aryl optionally substituted with 1 or 2 groups that are independently halogen, —$CF_3$, —$OCF_3$, —OH, $C_1-C_6$ alkoxy, —CN, —$CO_2H$, —SH, —$NO_2$, or NR'R", wherein R' and R" are independently H or $(C_1-C_6)$ alkyl.

Preferred compounds of the formula VIII-1 include those wherein $R_1$ is phenyl optionally substituted with 1 or 2 groups that are independently halogen, —$CF_3$, —$OCF_3$, —OH, $C_1-C_6$ alkoxy, —CN, —$CO_2H$, —SH, —$NO_2$, or NR'R", wherein R' and R" are independently H or $(C_1-C_6)$ alkyl; and $R_2$ is benzodioxolyl optionally substituted with 1 or 2 groups that are independently halogen, —$CF_3$, —$OCF_3$, —OH, $C_1-C_6$ alkoxy, —CN, —$CO_2H$, —SH, —$NO_2$, or NR'R", wherein R' and R" are independently H or $(C_1-C_6)$ alkyl.

Preferred compounds of the formula VIII-1 include those wherein $R_1$ is phenyl substituted with 1 or 2 OH groups.

Preferred compounds of the formula VIII-1 include those wherein $R_2$ is benzodioxolyl.

As noted above, the invention also provides compounds of formula (IX):

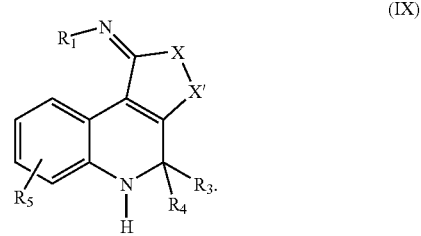

(IX)

Preferred compounds of formula (IX) include those of formula IX-1, i.e., compounds of formula (IX) wherein:

X and X' are both sulfur;

$R_1$ is cycloalkyl, aryl, heteroaryl or heterocycloalkyl, wherein each ring is optionally substituted with 1, 2, or 3 groups that are independently $(C_1-C_6)$ alkyl, halogen, haloalkyl, —$CF_3$, —$OCF_3$, —OH, $C_1-C_6$ alkoxy, hydroxyalkyl, —CN, —$CO_2H$, —SH, —S-alkyl, —$NO_2$, or NR'R", wherein R' and R" are independently H or $(C_1-C_6)$ alkyl;

$R_3$ and $R_4$ are independently H, or $(C_1-C_6)$ alkyl; and $R_5$ is H, $(C_1-C_6)$ alkyl, halogen, haloalkyl, —$CF_3$, —$OCF_3$, —OH, $C_1-C_6$ alkoxy, hydroxyalkyl, —CN, —$CO_2H$, —SH, —S-alkyl, —$NO_2$, or NR'R", wherein R' and R" are independently H or $(C_1-C_6)$ alkyl.

Preferred compounds of the formula IX-1 include those wherein $R_1$ is aryl optionally substituted with 1, 2 or 3 groups that are independently halogen, —$CF_3$, —$OCF_3$, —OH, $C_1-C_6$ alkoxy, —CN, —CO$_2$H, —SH, —NO$_2$, or NR'R", wherein R' and R" are independently H or (C$_1$–C$_6$) alkyl; and R$_3$ and R$_4$ are independently (C$_1$–C$_6$) alkyl; and R$_5$ is H, (C$_1$–C$_6$) alkyl, haloalkyl, C$_1$–C$_6$ alkoxy, or hydroxy-alkyl.

Preferred compounds of the formula IX-1 include those wherein

R$_1$ is phenyl optionally substituted with 1, 2 or 3 groups that are independently halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl; and R$_3$ and R$_4$ are independently (C$_1$–C$_6$) alkyl; and R$_5$ is H, (C$_1$–C$_6$) alkyl, haloalkyl, C$_1$–C$_6$ alkoxy, or hydroxy-alkyl.

Preferred compounds of the formula IX-1 include those wherein R$_1$ is phenyl substituted with 1 or 2-OH groups.

Preferred compounds of the formula IX-1 include those wherein R$_3$ and R$_4$ are independently (C$_1$–C$_3$) alkyl.

Preferred compounds of the formula IX-1 include those wherein R$_5$ is C$_1$–C$_6$ alkoxy.

As noted above, the invention also provides compounds of formula (X):

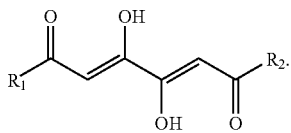

(X)

Preferred compounds of formula (X) include those of formula X-1, i.e., compounds of formula (X) wherein:

R$_1$ and R$_2$ are independently cycloalkyl, aryl, heteroaryl or heterocycloalkyl, wherein each ring is optionally substituted with 1, 2, or 3 groups that are independently (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl.

Preferred compounds of the formula X-1 include those wherein

R$_1$ and R$_2$ are independently aryl optionally substituted with 1 or 2 groups that are independently halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl.

Preferred compounds of the formula X-1 include those wherein

R$_1$ and R$_2$ are both phenyl each optionally substituted with 1 or 2 groups that are independently halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl.

Preferred compounds of the formula X-1 include those wherein R$_1$ and R$_2$ are both phenyl.

As noted above, the invention also provides compounds of formula (XI):

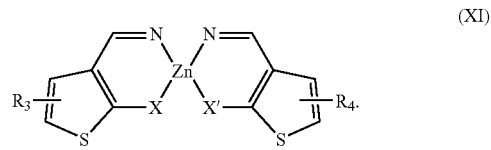

(XI)

Preferred compounds of formula (XI) include those of formula XI-1, i.e., compounds of formula (XI) wherein:

X and X' are both sulfur; and

R$_3$ and R$_4$ are independently H, (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl.

Preferred compounds of the formula XI-1 include those wherein

R$_3$ and R$_4$ are independently H, (C$_1$–C$_6$) alkyl, halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl.

Preferred compounds of the formula XI-1 include those wherein R$_3$ and R$_4$ are independently (C$_1$–C$_6$) alkyl.

Representative compounds of the invention include those in Table 1:

TABLE 1

Representative compounds of the invention.

| Cmpd. No. | Structure/Name |
|---|---|
| 1 | 5-(2,4-Dihydroxy-benzylidene)-3-(4-methoxy-phenyl)-2-thioxo-thiazolidin-4-one |

TABLE 1-continued
Representative compounds of the invention.
| Cmpd. No. | Structure/Name |
| --- | --- |
| 2 | 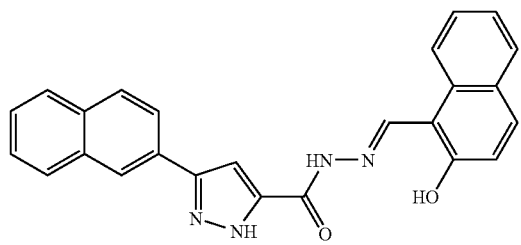<br>5-Naphthalen-2-yl-2H-pyrazole-3-carboxylic acid (2-hydroxy-naphthalen-1-ylmethylene)-hydrazide |
| 3 | 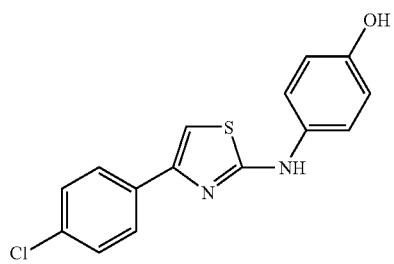<br>4-[4-(4-Chloro-phenyl)-thiazol-2-ylamino]-phenol |
| 4 | 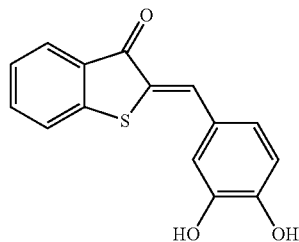<br>2-(3,4-Dihydroxy-benzylidene)-benzo [b] thiophen-3-one |
| 5 | 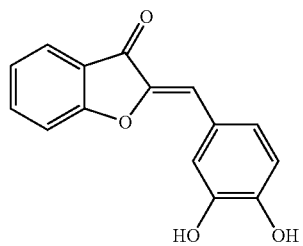<br>2-(3,4-Dihydroxy-benzylidene)-benzofuran-3-one |

TABLE 1-continued

Representative compounds of the invention.

| Cmpd. No. | Structure/Name |
|---|---|
| 6 | 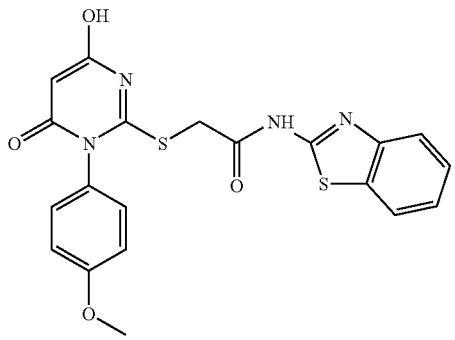<br>N-Benzothiazol-2-yl-2-[4-hydroxy-1-(4-methoxy-phenyl)-6-oxo-1,6-dihydro-pyrimidin-2-ylsulfanyl]-acetamide |
| 7 | 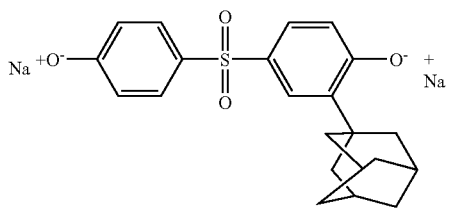<br>2-(1-adamantyl)-4-[(4-oxidophenyl) sulfonyl]benzenolate disodium salt |
| 8 | 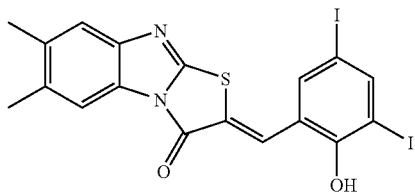<br>2-(2-Hydroxy-3,5-diiodo-benzylidene)-6,7-dimethyl-benzo[4,5] imidazo [2,1-b] thiazol-3-one |
| 9 | 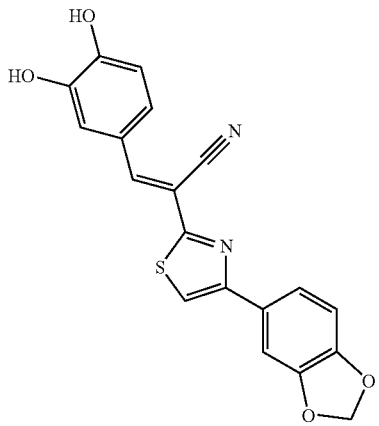<br>2-(4-Benzo[1,3]dioxol-5-yl-thiazol-2-yl)-3-(3,4-dihydroxy-phenyl)-acrylonitrile |

TABLE 1-continued

Representative compounds of the invention.

| Cmpd. No. | Structure/Name |
|---|---|
| 10 | 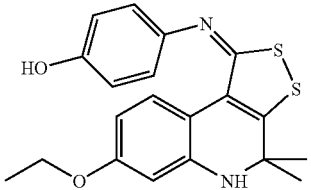<br>4-(7-Ethoxy-4,4-dimethyl-4,5-dihydro-2,3-dithia-5-aza-cyclopenta [α] naphthalen-1-ylideneamino)-phenol |
| 11 | 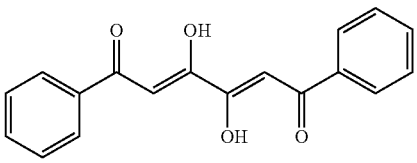<br>3,4-Dihydroxy-1,6-diphenyl-hexa-2,4-diene-1,6-dione |
| 12 | 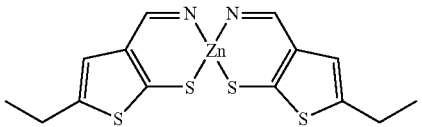 |

The invention also provides methods for treating an animal, including a human patient who has, or in preventing a patient from getting, a disease or condition that is a hyperproliferative disease, an autoimmune disease, an inflammatory disease, and allergy, which methods include the step of administering a therapeutically effective amount of a compound of formula (I) or a pharmaceutically acceptable salt thereof, administering a therapeutically effective amount of a compound of formula (II) or a pharmaceutically acceptable salt thereof, administering a therapeutically effective amount of a compound of formula (III) or a pharmaceutically acceptable salt thereof, administering a therapeutically effective amount of a compound of formula (IV) or a pharmaceutically acceptable salt thereof, administering a therapeutically effective amount of a compound of formula (V) or a pharmaceutically acceptable salt thereof, administering a therapeutically effective amount of a compound of formula (VI) or a pharmaceutically acceptable salt thereof, administering a therapeutically effective amount of a compound of formula (VII) or a pharmaceutically acceptable salt thereof, administering a therapeutically effective amount of a compound of formula (VIII) or a pharmaceutically acceptable salt thereof, administering a therapeutically effective amount of a compound of formula (IX) or a pharmaceutically acceptable salt thereof, administering a therapeutically effective amount of a compound of formula (X) or a pharmaceutically acceptable salt thereof, or administering a therapeutically effective amount of a compound of formula (XI) or a pharmaceutically acceptable salt thereof, to an animal, including a human patient, in need thereof. One preferred hyperproliferative disease for which the compounds of the invention and pharmaceutical formulations and compositions thereof are useful in treating or preventing is cancer, most particularly cancer that arises in a cell or tissue type that expresses SK, and also particularly in such a cancer that is resistant to chemotherapeutic, cytotoxic cytostatic, or antiproliferative drugs. Other preferred diseases that can be treated or prevented with the compounds of the invention include atherosclerosis, restenosis, psoriasis and rheumatoid arthritis.

The invention also provides pharmaceutical compositions which include a compound of formula (I) or a pharmaceutically acceptable salt thereof, a compound of formula (II) or a pharmaceutically acceptable salt thereof, a compound of formula (III) or a pharmaceutically acceptable salt thereof, a compound of formula (IV) or a pharmaceutically acceptable salt thereof, a compound of formula (V) or a pharmaceutically acceptable salt thereof, a compound of formula (VI) or a pharmaceutically acceptable salt thereof, a compound of formula (VII) or a pharmaceutically acceptable salt thereof, a compound of formula (VIII) or a pharmaceutically acceptable salt thereof, a compound of formula (IX) or a pharmaceutically acceptable salt thereof, a compound of formula (X) or a pharmaceutically acceptable salt thereof, or a compound of formula (XI) or a pharmaceutically acceptable salt thereof, as active ingredients, in combination with a pharmaceutically acceptable carrier, medium, or auxiliary agent.

The pharmaceutical compositions of the present invention may be prepared in various forms for administration, including tablets, caplets, pills or dragees, or can be filled in suitable containers, such as capsules, or, in the case of suspensions, filled into bottles. As used herein "pharmaceutically acceptable carrier medium" includes any and all solvents, diluents, or other liquid vehicle; dispersion or suspension aids; surface active agents; preservatives; solid binders; lubricants and the like, as suited to the particular dosage form desired. Various vehicles and carriers used in formulating pharmaceutical compositions and known techniques for the preparation thereof are disclosed in *Remington's Pharmaceutical Sciences* (A. Osol et al. eds., 15th ed. 1975). Except insofar as any conventional carrier medium is incompatible with the chemical compounds of the present invention, such as by producing any undesirable biological effect or otherwise interacting in a deleterious manner with any other component of the pharmaceutical composition, the use of the carrier medium is contemplated to be within the scope of this invention.

In the pharmaceutical compositions of the present invention, the active agent may be present in an amount of at least 1% and not more than 95% by weight, based on the total weight of the composition, including carrier medium or auxiliary agents. Preferably, the proportion of active agent varies between 1% to 70% by weight of the composition. Pharmaceutical organic or inorganic solid or liquid carrier media suitable for enteral or parenteral administration can be used to make up the composition. Gelatin, lactose, starch, magnesium, stearate, talc, vegetable and animal fats and oils, gum polyalkylene glycol, or other known excipients or diluents for medicaments may all be suitable as carrier media.

The pharmaceutical compositions of the present invention may be administered using any amount and any route of administration effective for treating a patient who has, or in preventing a patient from getting, a disease or condition selected from the group consisting of a hyperproliferative disease, an autoimmune disease, an inflammatory disease, and allergy. Thus the expression "therapeutically effective amount," as used herein, refers to a sufficient amount of the active agent to provide the desired effect against target cells. The exact amount required will vary from subject to subject, depending on the species, age, and general condition of the subject; the particular chemosensitizing agent; its mode of administration; and the like. As an example, a therapeutically effective amount can be about 0.1 mg to about 10,000 mg of the agent, with a range of about 1 mg to about 1000 mg being preferred.

The pharmaceutical compounds of the present invention are preferably formulated in dosage unit form for ease of administration and uniformity of dosage. "Dosage unit form," as used herein, refers to a physically discrete unit of therapeutic agent appropriate for the animal to be treated. Each dosage should contain the quantity of active material calculated to produce the desired therapeutic effect either as such, or in association with the selected pharmaceutical carrier medium. Typically, the pharmaceutical composition will be administered in dosage units containing from about 0.1 mg to about 10,000 mg of the agent, with a range of about 1 mg to about 1000 mg being preferred.

The pharmaceutical compositions of the present invention may be administered orally or paternally, such as by intramuscular injection, intraperitoneal injection, or intravenous infusion. The pharmaceutical compositions may be administered orally or parenterally at dosage levels of about 0.1 to about 1000 mg/kg, and preferably from about 1 to about 100 mg/kg, of animal body weight per day, one or more times a day, to obtain the desired therapeutic effect.

Although the pharmaceutical compositions of the present invention can be administered to any subject that can benefit from the therapeutic effects of the compositions, the compositions are intended particularly for the treatment of diseases in humans.

The pharmaceutical compositions of the present invention will typically be administered from 1 to 4 times a day, so as to deliver the daily dosage as described herein. Alternatively, dosages within these ranges can be administered by constant infusion over an extended period of time, usually 1 to 96 hours, until the desired therapeutic benefits have been obtained. However, the exact regimen for administration of the chemical compounds and pharmaceutical compositions described herein will necessarily be dependent on the needs of the animal being treated, the type of treatments being administered, and the judgment of the attending physician.

In certain situations, the compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

Non-toxic pharmaceutically acceptable salts of the compounds of the present invention include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of the present invention.

The invention also encompasses prodrugs of the compounds of the present invention. Those skilled in the art will recognize various synthetic methodologies, which may be employed to prepare non-toxic pharmaceutically acceptable addition salts and prodrugs of the compounds encompassed by the present invention.

The invention provides compounds of formula I, II, III, IV, V, VI, VII, VIII, IX, X, and XI that are inhibitors of SK, and which are useful for modulating the sphingomyelin signal transduction pathway, and in treating and preventing hyperproliferative diseases, autoimmune diseases, inflammatory diseases, and allergy. The compounds of the invention can be prepared by one skilled in the art based only on knowledge of the compound's chemical structure. The chemistry for the preparation of the compounds of this invention is known to those skilled in the art. In fact, there is more than one process to prepare the compounds of the invention. Specific examples of methods of preparation can be found herein and in the art.

As discussed above, sphingolipids are critically important in regulating the balance between cell proliferation and apoptosis. Sphingosine 1-phosphate (S1P) is produced by the enzyme SK and stimulates the proliferation of tumor cells. Concurrent depletion of ceramide by the action of SK blocks apoptosis. Therefore, inhibition of SK activity according to the invention will attenuate tumor cell proliferation and promote apoptosis.

The compounds of the invention are inhibitors of SK that are demonstrated herein to specifically inhibit kinase activity of recombinant human SK and are more potent than any other prior art SK inhibitor. In addition, preferred compounds of the invention generally do not compete for the ATP binding site of the enzyme.

The compounds of the invention are cytotoxic toward tumor cells, including cell lines with the multidrug resistance phenotype. Therefore, the compounds of the invention are anticancer agents having a unique molecular target. Since cell hyperproliferation is a required process in the development of atherosclerosis and psoriasis, the compounds of the invention, which are SK inhibitors, are useful in the treatment of these diseases. Additionally, it is believed that inappropriate activation and/or proliferation of specific classes of lymphocytes results in chronic inflammatory and autoimmune diseases. Consequently, compounds of the invention are also useful in the treatment of these diseases.

Definitions

The definitions and explanations below are for the terms as used throughout this entire document including both the specification and the claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The symbol "—" in general represents a bond between two atoms in the chain. Thus $CH_3$—O—$CH_2$—$CH(R_t)$—$CH_3$ represents a 2-substituted-1-methoxypropane compound. In addition, the symbol "—" represents the point of attachment of the substituent to a compound. Thus for example aryl($C_1$–$C_6$)alkyl- indicates an alkylaryl group, such as benzyl, attached to the compound at the alkyl moiety.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

A "therapeutically effective" amount is defined as an amount effective to reduce or lessen at least one symptom of the disease being treated or to reduce or delay onset of one or more clinical markers or symptoms of the disease.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

The term "alkyl" includes those alkyl groups of a designed number of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like.

By the term "halogen" in the present invention is meant fluorine, bromine, chlorine, and iodine.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and biphenyl.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl, cyclohexyl and cycloheptyl. The cycloalkyl groups herein are unsubstituted or, as specified, substituted in one or more substitutable positions with various groups. Examples of cycloalkyl include cyclopropyl, cyclobutyl, cyclopentyl, cyclohexyl, cycloheptyl, cyclooctyl and adamantyl.

The term "cycloalkylalkyl," as used herein, refers to a $C_3$–$C_7$ cycloalkyl group attached to the parent molecular moiety through an alkyl group, as defined above. Examples of cycloalkylalkyl groups include cyclopropylmethyl and cyclopentylethyl.

The terms "halogen" or "halo" indicate fluorine, chlorine, bromine, or iodine.

The term "heterocycloalkyl," refers to a non-aromatic ring system containing at least one heteroatom selected from nitrogen, oxygen, and sulfur. The heterocycloalkyl ring may be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrolidinyl.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

All patents and publications referred to herein are hereby incorporated by reference for all purposes.

Structures were named using Chemdraw Ultra, version 6.0.2, available from CambridgeSoft, 100 CambridgePark Drive, Cambridge, Mass. 02140, USA, or with Name Pro IUPAC Naming Software, version 6.00, available from Advanced Chemical Development, Inc., 90 Adelaide Street West, Toronto, Ontario, M5H 3V9, Canada.

The present invention may be better understood with reference to the following examples. These examples are intended to be representative of specific embodiments of the invention, and are not intended as limiting the scope of the invention.

BIOLOGY EXAMPLES

General

Compounds 1–4 and 6–12 were purchased, as part of a chemical library, from Chembridge Corporation (San Diego, Calif.). Compound 5 was prepared as described below.

Sphingosine Kinase Screen

A medium-throughput assay for screening for inhibitors of recombinant human SK was used. cDNA for human SK was subcloned into a PGEX bacterial expression vector (Pharmacia), which resulted in expression of the enzyme as a fusion protein with glutathione-S-transferase. The fusion protein was then purified on a column of immobilized reduced glutathione (GSH), and the activity measured according to the method of Louie (as described in the *Journal of Biological Chemistry*, 1976, Vol. 251, 4557–4764). This method involved incubating [$^3$H]sphingosine with 1 mM ATP under conditions defined in the reference, followed by extraction of the assay mixture with chloroform:methanol (2:1) under basic conditions. This resulted in partitioning of the unreacted [$^3$H]sphingosine into the organic phase, while S1P partitioned into the aqueous phase. Radioactivity in aliquots of the aqueous phase was then quantified as a measure of [$^3$H]S1P formation. There was a low background level of partitioning of [$^3$H] sphingosine into the aqueous phase, and addition of the recombinant SK greatly increased the formation of [$^3$H]S1P. The intra-assay coefficient of variation was below 10%, while interassay variation was approximately 20%. A positive control, dimethylsphingosine, completely inhibited SK activity at concentrations above 25 μM. In contrast, DMSO solvent did not inhibit SK activity. The screening assays were conducted at a fixed concentration of 5 μg of test compound/ml, which corresponded to concentrations of 10–25 μM.

Characterization of Novel SK Inhibitors

Compounds 1, 2, 3, and 4 from Table 1 (at 5 μg/ml) inhibited SK activity by 99, 85, 99 and 89%, respectively. These four compounds were evaluated in more detail as described below. In addition, compounds 5–12 were also found to inhibit SK activity. Concentrations of 5 μg/ml of compounds 5, 6, 7, 8, 9, 10, 11 or 12 inhibited SK activity by 90, 91, 91, 98, 94, 81, 98, and 87%, respectively.

Figure 2:
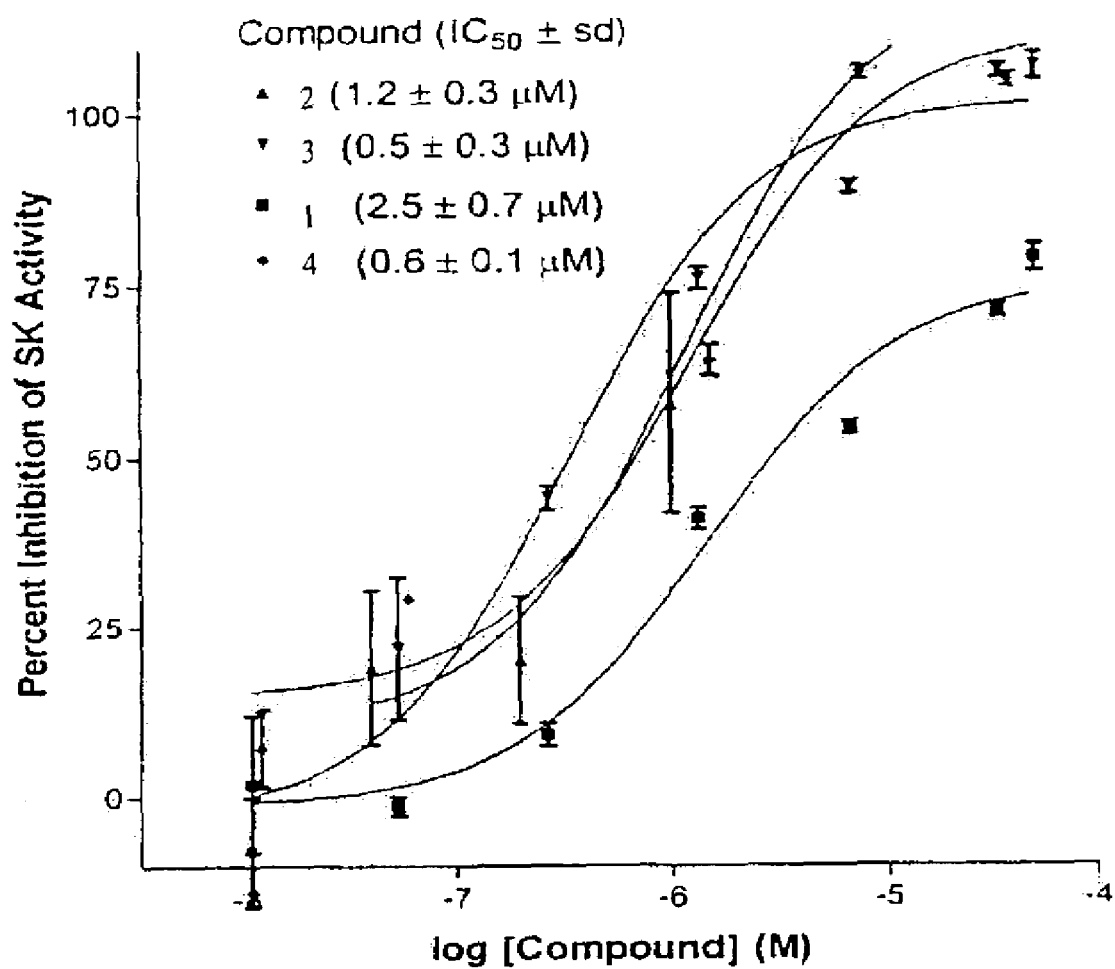
FIG. 2 depicts dose response curves for inhibition of SK by compounds of the invention.

While the screen provided rapid identification of compounds that inhibited SK activity, it provided information at only one inhibitor concentration. Therefore, the effects of Compounds 1–4 were determined at multiple concentrations and IC$_{50}$ values for each compound were calculated. Varying concentrations of the indicated compounds were evaluated for inhibition of recombinant human SK as described above. The data is shown in FIG. 2. Data points represent the results ±the standard deviation (SD) of triplicate samples, from which best-fit lines from regression analyses were plotted. The calculated IC$_{50}$ (μM) for each compound is indicated in the insert (FIG. 2).

As summarized in FIG. 2, all of the compounds demonstrated IC$_{50}$s in the sub-to low-micromolar range. Consequently, all four compounds are more potent inhibitors of SK than any previously reported compound.

An important feature of these compounds relates to the mechanism for their inhibition of SK. Specifically, it was determined that these inhibitors did not compete for binding with the ATP binding site. Significantly, it was recognized that compounds that bind to the ATP binding site may not be specific for SK, which could cause undesired cross-inhibition of other ATP-dependent enzymes. Indeed, this is a common problem with development of selective protein kinase inhibitors.

Figure 3:
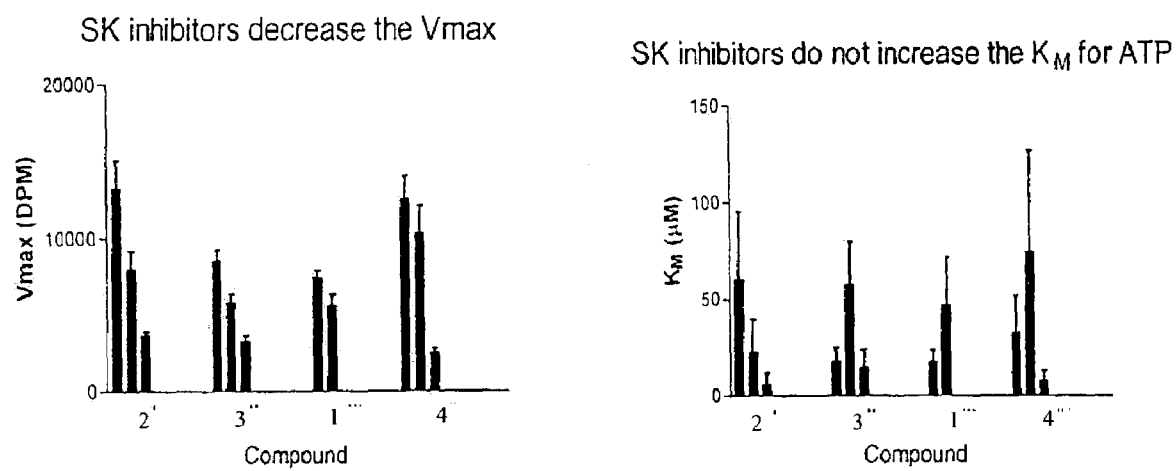
FIG. 3 are graphs showing kinetic parameters for purified human SK in the presence of compounds of the invention.

Competition assays were performed in which sphingosine and SK concentrations were held constant, and ATP and inhibitor concentrations were varied. For each concentration of inhibitor, the K$_M$ for ATP and the V$_{max}$ for the reaction were determined. The data for Compounds 1–4 are summarized in FIG. 3. Compounds that compete for the ATP binding site were expected to increase the K$_M$ for ATP without affecting the V$_{max}$ of the reaction. The V$_{max}$ values showed consistent decreases with increasing concentrations of any of the test compounds. In the same experiments, the K$_M$ for ATP had a tendency to decrease, but certainly does not increase with increasing concentration of the inhibitors. These results demonstrated that compounds 1–4 exerted their inhibitory effects by binding to a site other than the ATP binding site of SK.

Selectivity of SK Inhibitors

The selectivity of the compounds of the invention towards SK was demonstrated by evaluating the effects of compounds on a panel of human protein kinases (ERK2 and PKC-α) and a lipid kinase (PI-3-kinase). Thus potencies of each inhibitor were determined for human isoforms of ERK2, PI3K and PKCα. SK inhibition data is provided for comparison. Data represent the concentrations required to inhibit enzyme activity by 50%, and are the mean ±SD of triplicate experiments. Results designated as "None" indicate that no inhibition was detected at concentrations up to 60 μM. The results are summarized in Table 2.

TABLE 2

In vitro potencies of SK inhibitors of against various kinases.

| Compound | SK | ERK2 | PI3K | PKCα |
|---|---|---|---|---|
| 1 | 2.5 ± 0.7 | 26 ± 2 | 42 ± 10 | None |
| 2 | 1.2 ± 0.3 | 11 ± 1 | None | None |
| 3 | 0.5 ± 0.3 | None | None | None |
| 4 | 0.6 ± 0.1 | 40 ± 5 | 7 ± 2 | None |
| 5 | 2.0 ± 0.2 | 80 ± 4 | 6 ± 2 | None |

As shown in Table 2, all five compounds tested demonstrated highest potency toward SK, with most having no inhibition of the other kinases at any concentration tested. Compound 2 showed some activity toward ERK2, but only at 10-fold higher concentrations than those required to inhibit SK. Compound 3 was the most selective as no inhibition was seen with any of the kinases tested. Compound 1 was 10- to 20-fold less potent toward ERK2 and PI3K than SK. Compound 4 and its analog Compound 5, had weak activity toward ERK2 and moderate activity toward PI3K. None of the compounds inhibited PKCα. Thus, while modest inhibition of certain other kinases was observed, these compounds demonstrated an acceptable degree of selectivity towards SK.

Cytotoxicity Profiles of SK Inhibitors

The SK inhibitor compounds of the invention are antiproliferative and induce apoptosis in replicating cells. In order to assess the compounds' efficacy in intact cells, the compounds were evaluated for cytotoxicity using a panel of human cancer cell lines. These experiments followed methods that have been extensively used (see for, example, Smith et al., *Cancer Res.* 54: 3779–3784 (1994); Smith et al., *Oncology Res.* 6: 211–218 (1994); and Lawrence et al., *J. Med. Chem.* 44: 594–601 (2001). Cell lines tested included T-24 human bladder carcinoma cells, MCF-7 human breast adenocarcinoma cells, MCF-7/VP cells, which are a subline of MCF-7 cells that is resistant to several anticancer drugs due to overexpression of the transport protein MRP 1, and NCI/ADR, a cell line resistant to many anticancer drugs due to overexpression of the drug transporter P-glycoprotein.

The cytotoxicities of compounds 1–4 are summarized in Table 3. The indicated cell lines were treated with varying doses of compounds 1–4 for 48 h. Cell survival was then determined using the SRB binding assay (Skehan et al., 1990, *J. Natl. Cancer Inst.* 82: 1107–1112), and the concentration of compound that inhibited proliferation by 50% was calculated. Values represent the mean ±SD for replicate samples.

The $IC_{50}$ values (in μM) in Table 3 indicate the concentration of Compound that inhibited tumor cell proliferation by 50%. As the data shows, these compounds were found to be antiproliferative at sub-to-low-micromolar concentrations that correspond quite well with the $IC_{50}$s for inhibiting SK activity in vitro. These results indicated that these compounds were able to enter tumor cells. Importantly, SK-inhibiting compounds of the invention were effective against tumor cells demonstrating the multidrug resistance phenotype due to overexpression of either P-glycoprotein or MRP 1. As these transporters are often overexpressed in tumor cells, particularly after the patient has been treated with cytotoxic drugs, the SK inhibiting compounds of the invention are effective therapeutic agents for resistant tumors.

TABLE 3

Cytotoxicities of SK inhibitors.

| Compound | Cell Line | | | |
|---|---|---|---|---|
| | T24 | MCF-7 | NCI/ADR | MCF-7/VP |
| | | $IC_{50}$ (μM) | | |
| 1 | 5.8 ± 1.5 | 6.8 ± 1.5 | 6.2 ± 1.5 | 24.6 ± 1.9 |
| 2 | 1.1 ± 1.2 | 0.4 ± 2.3 | 0.8 ± 1.3 | 2.9 ± 2.0 |
| 3 | 4.6 ± 1.6 | 1.2 ± 1.3 | 1.3 ± 1.1 | 0.9 ± 1.8 |
| 4 | 7.8 ± 2.0 | 1.0 ± 1.7 | 1.2 ± 2.4 | 1.8 ± 1.1 |

Antitumor Activity

Antitumor activity was assessed by determining the effects of Compound 5 (2-(3,4-Dihydroxy-benzylidene)-benzofuran-3-one) in a syngeneic tumor model using the mouse JC mammary adenocarcinoma cells growing subcutaneously in immunocompetent Balb/c mice. These cells express elevated levels of SK activity relative to non-transformed cells, as well as the multidrug resistance phenotype due to P-glycoprotein activity (data not shown).

Figure 4:
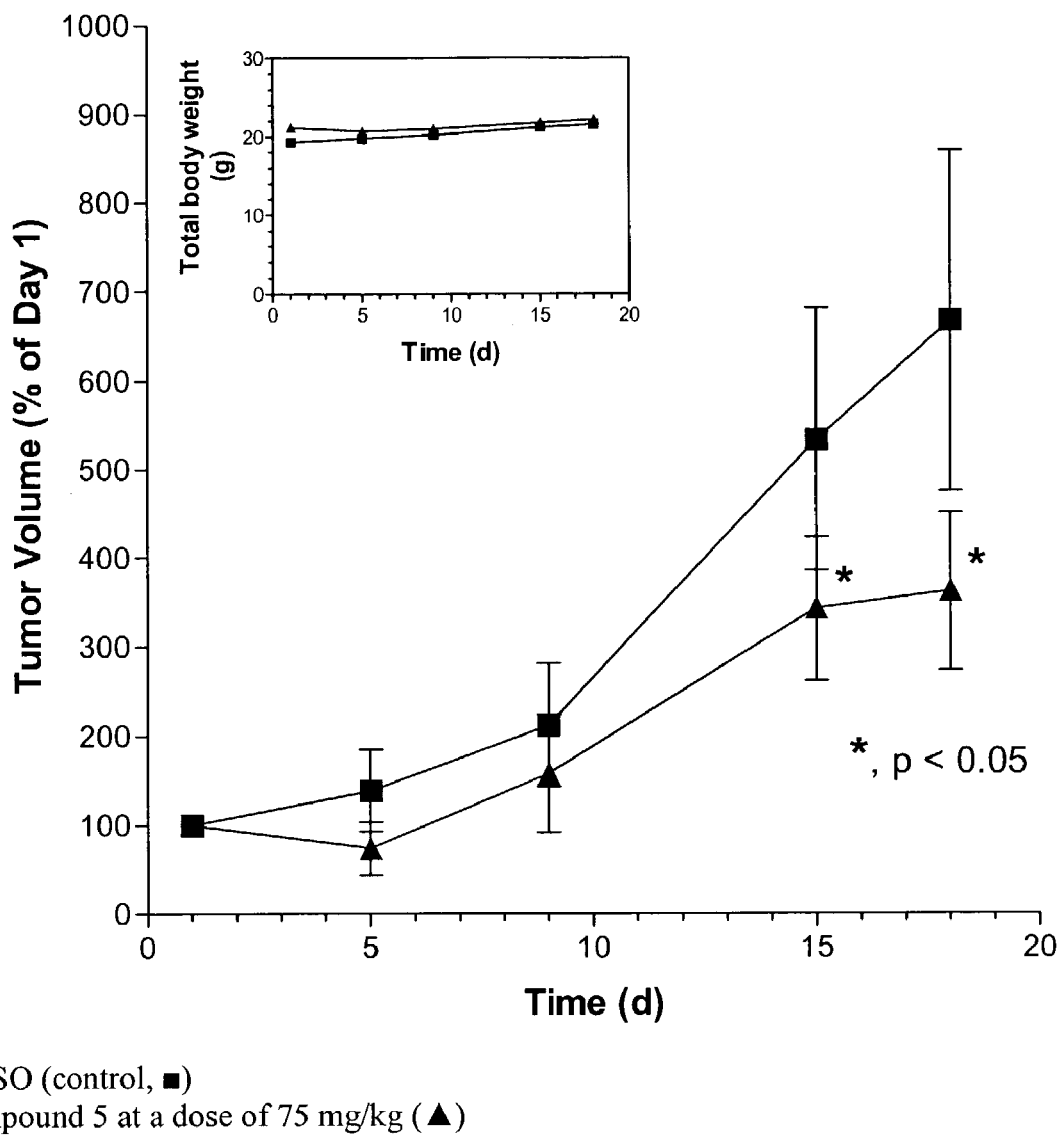
FIG. 4 is a graph showing antitumor activity of compound 5.

The data are shown in FIG. 4. Balb/c mice, 6–8 weeks old, were injected subcutaneously with $10_6$ JC cells suspended in PBS. DMSO (control, shown as a black square) or Compound 5 at a dose of 75 mg/kg (shown as a black diamond) was administered intraperitoneally on days 1, 5, 9 and 15. Tumor growth is expressed as the volume relative to day 1 for each animal. Asterisks indicate P-values<0.05, determined by unpaired t-tests. The insert indicates the body weight of the animals during this experiment.

As indicated in FIG. 4, tumor growth in animals treated with Compound 5 was significantly lower (>50% decreased at day 18) than tumor growth in control animals. No significant difference in the body weights of animals in the two groups was observed, indicating the lack of overt toxicity from Compound 5.

CHEMISTRY EXAMPLES

Example 1

Synthesis of 5-Naphthalen-2-yl-2H-pyrazole-3-carboxylic Acid (2-hydroxy-naphthalen-1-ylmethylene)-hydrazide (table 1, compound 2)

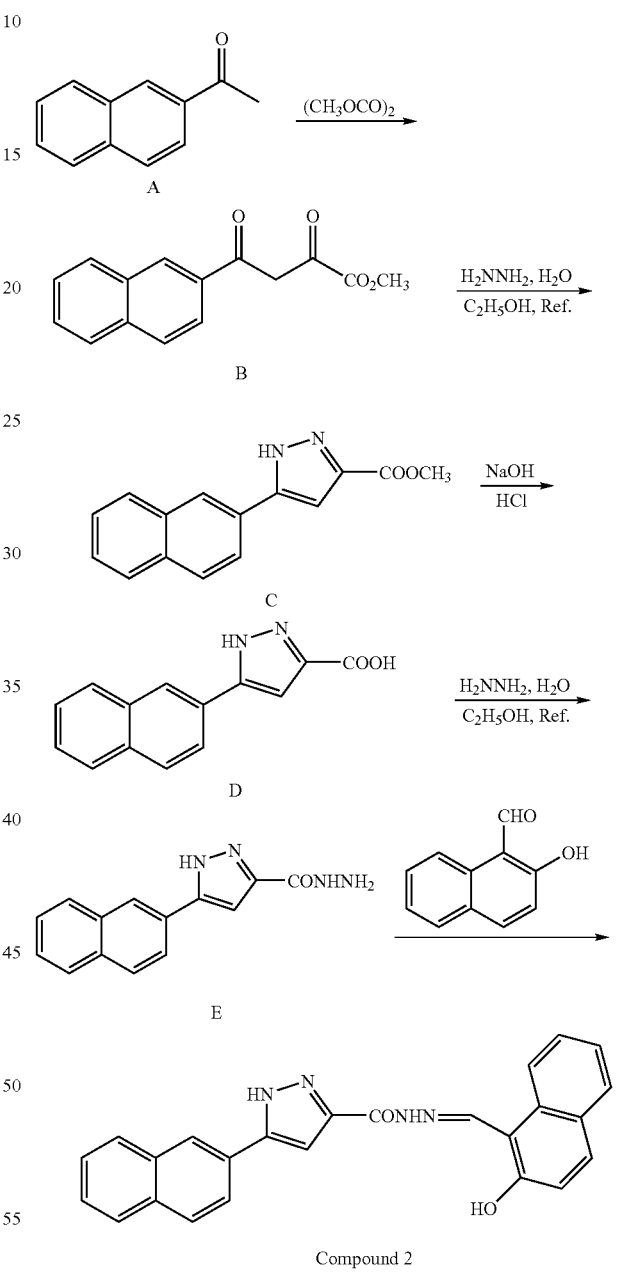

Compound 2

Condensation of 2-acetylnaphthalene (A) with dimethyl oxalate gave methyl butenoate (B) (J. Med. Chem. 1983, 26, 1196–1200). Ester (B) was reacted with hydrazine to give carbomethoxy substituted pyrazole (C) (J. Med. Chem. 1995, 38, 617–628). Saponification of (C) gave (D). Ester (D) was reacted with hydrazine to give (5). Followed by reaction with 2-Hydroxy-naphthalene-1-carbaldehyde yield the target compound (J. Org. Chem. 1990, 55, 1070–1076).

Example 2

Synthesis of 2-(3,4-Dihydroxy-benzylidene)-benzofuran-3-one (table 1, compound 5)

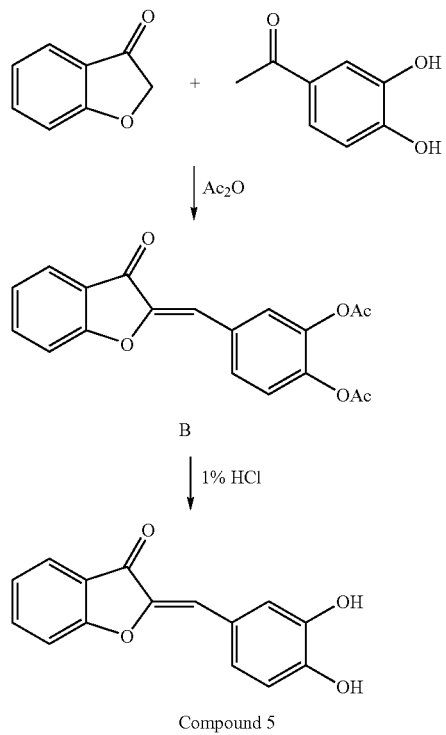

Compound 5

Benzofuran-3-one exists in equilibrium, between the keto- and enol-tautomers and underwent an aldol condensation with 3,4-dihydroxy-benzaldehyde in acetic anhydride to form 3,4-diacetoxyaurone (B). Hydrolysis of B in a mild hydrochloric acid solution gave 2-(3,4-dihydroxy-benzylidene)-benzofuran-3-one (Compound 5). For these reactions solvents were dried and distilled before use, and reactions requiring anhydrous conditions were conducted under an atmosphere of nitrogen. Purifications were done by column chromatography on silica (Merck, silica gel 60, 230–400 mesh). The identities of B and Compound 5 were verified by NMR spectroscopy on a Bruker 200 MHz instrument. Chemical shifts relative to trimethylsilane for $^1$H- and $^{13}$C-NMR spectra follow. Mass spectral data were provided by Mass Consortium (San Diego). For 3,4-diacetoxyaurone (B): $^1$H NMR(200 MHz, CDCl$_3$) δ 2.32–2.35 (s,s, 6H, 2CH$_3$), 6.82 (s, 1H, HC═), 7.24–7.36 (m, 3H, Ar—H), 7.67–7.83 (m, 4H, Ar—H); $^{13}$C NMR(200 MHz, CDCl$_3$) δ 20.65, 20.69, 111.0, 113.0, 123.7, 123.9, 124.8, 126.0, 129.9, 130.9, 131.2, 137.1, 142.5, 147.2, 166.2; MS m/z (rel intensity) 339 (MH$^+$, 30), 297 (100), 255 (40). For 2-(3,4-dihydroxy-benzylidene)-benzofuran-3-one (Compound 5): $^1$H NMR(200 MHz, Acetone-d$_6$) δ 6.75 (s, 1H, HC═), 6.94–6.98 (d, J=8 Hz, 1H, Ar—H), 7.31–7.49 (m, 3H, Ar—H), 7.63 (s, 1H, Ar—H), 7.74–7.81 (m, 2H, Ar—H), 8.32 (s, 1H, OH), 8.65 (s,1H, OH); $^{13}$C NMR(200 MHz, CDCl$_3$) δ 114.5, 114.6, 117.4, 119.8, 125.1, 125.6, 126.9, 138.3; MS m/z (rel intensity) 255 (MH$^+$, 100).

A diverse set of substituted aurones can be efficiently synthesized by condensation of benzofuran-3-one with an aldehyde. This method works well with both aromatic and non-aromatic aldehydes, and a variety of such aldehydes are commercially available.

It should be understood that the foregoing disclosure emphasizes certain specific embodiments of the invention and that all modifications or alternatives equivalent thereto are within the spirit and scope of the invention as set forth in the appended claims.

What is claimed is:

1. A pharmaceutical composition comprising a compound or salt of formula (VIII):

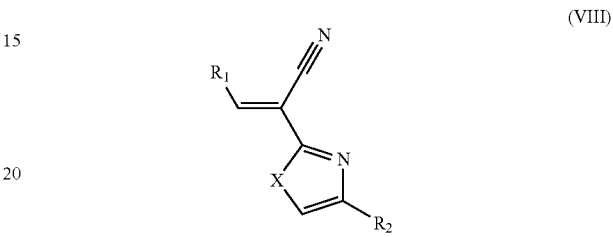

(VIII)

and a pharmaceutically acceptable carrier, wherein
X is sulfur;
R$_1$ is cycloalkyl, or aryl, wherein each ring is optionally substituted with 1, 2, or 3 groups that are independently (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl; and
R$_2$ is cycloalkyl, or aryl, wherein each ring is optionally substituted with 1, 2, or 3 groups that are independently (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl or R$_2$ is benzodioxolyl optionally substituted with 1 or 2 groups that are independently halogen, —CF$_3$, —OCF$_3$, —OH, C$_1$–C$_6$ alkoxy, —CN, —CO$_2$H, —SH, —NO$_2$, or NR'R", wherein R' and R" are independently H or (C$_1$–C$_6$) alkyl.

2. The pharmaceutical composition of claim 1 wherein the compound is 2-(4-Benzo[1,3]dioxol-5-yl-thiazol-2-yl)-3-(3,4-dihydroxy-phenyl)-acrylonitrile, or a pharmaceutically acceptable salt thereof.

3. A method for inhibiting sphingosine kinase in a cell, the method comprising administering a therapeutically effective amount of a sphingosine kinase inhibitor of formula I-1

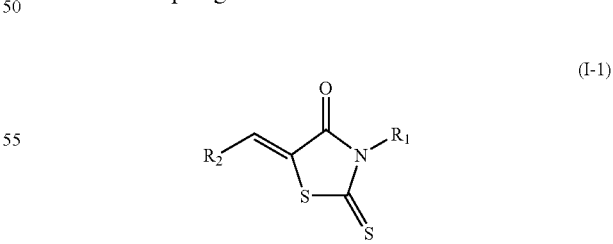

(I-1)

or a pharmaceutically acceptable salt thereof, wherein
R$_1$ is cycloalkyl, or aryl, wherein each ring is optionally substituted with 1, 2, or 3 groups that are independently (C$_1$–C$_6$) alkyl, halogen, haloalkyl, —CF$_3$, —OCF$_3$, —OH, C$_1$–C$_6$ alkoxy, hydroxyalkyl, —CN, —CO$_2$H, —SH, —S-alkyl, —NO$_2$, or NR'R", wherein R' and R" are independently H or (C$_1$–C$_6$) alkyl; and R₂ is cycloalkyl, or aryl, wherein each ring is optionally substituted with 1, 2, or 3 groups that are independently $(C_1-C_6)$ alkyl, halogen, haloalkyl, —CF₃, —OCF₃, —OH, $C_1-C_6$ alkoxy, hydroxyalkyl, —CN, —CO₂H, —SH, —S-alkyl, —NO₂, or NR'R", wherein R' and R" are independently H or $(C_1-C_6)$ alkyl.

4. The method of claim 3 wherein the sphingosine kinase inhibitor is 5-(2,4-Dihydroxy-benzylidene)-3-(4-methoxy-phenyl)-2-thioxo-thiazolidin-4-one.

5. A method for inhibiting sphingosine kinase in a cell, the method comprising administering a therapeutically effective amount of a sphingosine kinase inhibitor of formula (III):

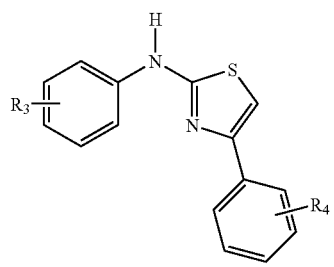

(III)

or a pharmaceutically acceptable salt thereof, wherein
R₃ is H, $(C_1-C_6)$ alkyl, halogen, haloalkyl, —CF₃, —OCF₃, —OH, $C_1-C_6$ alkoxy, hydroxyalkyl, —CN, —CO₂H, —SH, —S-alkyl, —NO₂, or NR'R", wherein R' and R" are independently H or $(C_1-C_6)$ alkyl; and
R₄ is H, $(C_1-C_6)$ alkyl, halogen, haloalkyl, —CF₃, —OCF₃, —OH, $C_1-C_6$ alkoxy, hydroxyalkyl, —CN, —CO₂H, —SH, —S-alkyl, —NO₂, or NR'R", wherein R' and R" are independently H or $(C_1-C_6)$ alkyl.

6. The method of claim 5 wherein the sphingosine kinase inhibitor is 4-[4-(4-Chloro-phenyl)-thiazol-2-ylamino]-phenol.

7. A method for inhibiting sphingosine kinase in a cell, the method comprising administering a therapeutically effective amount of a sphingosine kinase inhibitor of formula (VIII):

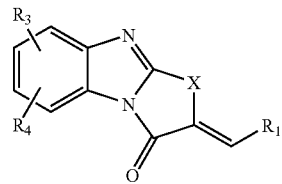

(VII)

or a pharmaceutically acceptable salt thereof, wherein
X is sulfur;
R₁ is cycloalkyl, or aryl, wherein each ring is optionally substituted with 1, 2, or 3 groups that are independently $(C_1-C_6)$ alkyl, halogen, haloalkyl, —CF₃, —OCF₃, —OH, $C_1-C_6$ alkoxy, hydroxyalkyl, —CN, —CO₂H, —SH, —S-alkyl, —NO₂, or NR'R", wherein R' and R" are independently H or $(C_1-C_6)$ alkyl; and
R₂ is cycloalkyl, or aryl, wherein each ring is optionally substituted with 1, 2, or 3 groups that are independently $(C_1-C_6)$ alkyl, halogen, haloalkyl, —CF₃, —OCF₃, —OH, $C_1-C_6$ alkoxy, hydroxyalkyl, —CN, —CO₂H, —SH, —S-alkyl, —NO₂, or NR'R", wherein R' and R" are independently H or $(C_1-C_6)$ alkyl, or R₂ is benzodioxolyl optionally substituted with 1 or 2 groups that are independently halogen, —CF₃, —OCF₃, —OH, $C_1-C_6$ alkoxy, —CN, —CO₂H, —SH, —NO₂, or NR'R", wherein R' and R" are independently H or $(C_1-C_6)$ alkyl.

8. The method of claim 7 wherein the sphingosine kinase inhibitor is 2-(4-Benzo[1,3]dioxol-5-yl-thiazol-2-yl)-3-(3, 4-dihydroxy-phenyl)-acrylonitrile.

* * * * *